US012734183B2

(12) United States Patent
Zaltzman

(10) Patent No.: US 12,734,183 B2
(45) Date of Patent: Sep. 15, 2026

(54) PHARMACEUTICAL COMPOSITIONS FOR RELIEF OF COVID-19 SYMPTOMS AND METHODS OF PRODUCING AND USING THEM

(71) Applicants: Pinchas Zaltzman, Bnei Brak (IL); Zahava Zaltzman, Bnei Brak (IL)

(72) Inventor: Pinchas Zaltzman, Bnei Brak (IL)

(73) Assignees: Pinchas Zaltzman, Bnei Brak (IL); Zahava Zaltzman, Bnei Brak (IL)

( * ) Notice: Subject to any disclaimer, the term of this patent is extended or adjusted under 35 U.S.C. 154(b) by 731 days.

(21) Appl. No.: 17/921,474

(22) PCT Filed: Apr. 27, 2021

(86) PCT No.: PCT/IL2021/050486
§ 371 (c)(1),
(2) Date: Oct. 26, 2022

(87) PCT Pub. No.: WO2021/220273
PCT Pub. Date: Nov. 4, 2021

(65) Prior Publication Data

US 2023/0190772 A1 Jun. 22, 2023

(30) Foreign Application Priority Data

Apr. 28, 2020 (IL) ......................................... 274327

(51) Int. Cl.
*A61K 31/65* (2006.01)
*A61K 9/10* (2006.01)
*A61K 33/22* (2006.01)
*A61K 35/644* (2015.01)
*A61K 36/28* (2006.01)
*A61P 31/14* (2006.01)

(52) U.S. Cl.
CPC ................ *A61K 31/65* (2013.01); *A61K 9/10* (2013.01); *A61K 33/22* (2013.01); *A61K 35/644* (2013.01); *A61K 36/28* (2013.01); *A61P 31/14* (2018.01)

(58) Field of Classification Search
CPC ....... A61P 31/14; A61K 31/65; A61K 35/644; A61K 36/28
See application file for complete search history.

(56) References Cited

U.S. PATENT DOCUMENTS

2004/0235047 A1* 11/2004 Siber ........................ A61P 31/14
435/7.1
2007/0184013 A1* 8/2007 Snyder ................. A61K 31/045
424/78.3
2014/0144429 A1* 5/2014 Wensley ............... A61M 15/06
128/200.14

FOREIGN PATENT DOCUMENTS

UA 106737 C2 * 10/2014
WO WO-2004112819 A1 * 12/2004 ............. A61K 36/00
WO 2020072850 A1 4/2020

OTHER PUBLICATIONS

English machine translation of UA-106737-C2 made Jul. 18, 2025. (Year: 2025).*
Yarnell, E., "Herbs for Viral Respiratory Infections." Alternative and Complementary Therapies, Feb. 2018, 24(1): 35-44.
Cao, B., et al., "A Trial of Lopinavir-Ritonavir in Adults Hospitalized with Severe Covid-19." The New England Journal of Medicine, 2020, 382(19): 1787-1799.
Lu, R., et al., "Genomic characterisation and epidemiology of 2019 novel coronavirus: implications for virus origins and receptor binding." The Lancet, 2020, 395: 565-574.
Mehta, P, et al., "COVID-19: consider cytokine storm syndromes and immunosuppression." The Lancet, 2020, 395: 1033-1034.
Wrapp, D., et al., "Cryo-EM structure of the 2019-nCoV spike in the prefusion conformation." Science, 2020, 367: 1260-1263.

* cited by examiner

*Primary Examiner* — Michael B. Pallay
(74) *Attorney, Agent, or Firm* — SALIWANCHIK, LLOYD & EISENSCHENK

(57) ABSTRACT

A pharmaceutical composition including: (a) a tetracycline family antibiotic, sodium tetraborate decahydrate, Calendula oil, Propolis, *Echinacea* sp. tincture; and (b) a liquid carrier comprising glycerin and ethanol.

3 Claims, 2 Drawing Sheets

PHARMACEUTICAL COMPOSITIONS FOR RELIEF OF COVID-19 SYMPTOMS AND METHODS OF PRODUCING AND USING THEM

CROSS REFERENCE TO RELATED APPLICATIONS

This application is a National Stage Application of International Application Number PCT/IL2021/050486, filed Apr. 27, 2021; which claims priority to Israel Patent Application No. 274327, filed on Apr. 28, 2020, both of which are incorporated herein in their entirety.

DETAILS OF RELATED APPLICATIONS

This PCT application claims priority under the Paris convention from Israeli Application IL 274327 entitled "ANTIVIRAL PREPARATIONS" filed on Apr. 28, 2020. IL 274327 comprises an inseparable part of the written record of this PCT application and is fully incorporated herein by reference.

FIELD OF THE INVENTION

The invention is in the field of pharmaceutical compositions.

BACKGROUND OF THE INVENTION

The present COVID-19 pandemic has flooded health care facilities with patients afflicted with symptoms of the virus. The symptoms include respiratory tract effects (e.g. shortness of breath or difficulty breathing, severe acute respiratory syndrome), high fever, and loss of senses of taste and/or smell. The reaction of each patient to the virus is individual and varies according to many factors, including age and background illnesses.

While vaccines have been developed, the vaccines are expensive and not available to many people in many countries. Alternatively or additionally, the vaccine may not be completely efficient against infection, and many people will benefit from symptomatic relief.

SUMMARY OF THE INVENTION

A broad aspect of the invention relates to relief of symptoms of COVID-19.

One aspect of some embodiments of the invention relates to a pharmaceutical composition (PC) for relief of COVID-19 symptoms. In some embodiments the pharmaceutical composition includes a broad spectrum antibiotic (e.g. a tetracycline family member), sodium tetraborate decahydrate (or an equivalent borate salt), Calendula oil, Propolis, and *Echinacea* (e.g. *angustifolia* and/or *purpurea*) tincture in a liquid carrier. In some exemplary embodiments of the invention, the liquid carrier includes an edible polyol (e.g. glycerol) and/or ethanol and/or water.

According to various exemplary embodiments of the invention the tetracycline family antibiotic includes Tetracycline and/or Doxycycline and/or Oxytetracycline and/or Clorotetracycline and/or other Chemically Modified Tetracyclines.

In some exemplary embodiments of the invention, one or more ingredients of the PC acts as an adjuvant.

In some embodiments the PC comprises at least 0.05%, at least 0.1%, at least 0.25%, at least 0.5%, at least 0.75%, at least 1.0% antibiotic or intermediate or greater percentages of antibiotic. Alternatively or additionally, in some embodiments the PC comprises not more than 2.0%, not more than 1.75%, not more than 1.5%, not more than 1.25%, not more than 1.0%, not more than 0.75%, not more than 0.5%, not more than 0.25%, or lesser or intermediate percentages of antibiotic.

In some embodiments the PC comprises at least 2.5%, at least 2.75%, at least 3.0%, at least 3.25%, at least 3.75%, at least 4.0% sodium tetraborate decahydrate or intermediate or greater percentages of sodium tetra borate decahydrate. Alternatively or additionally, in some embodiments the PC comprises not more than 5.0%, not more than 4.75%, not more than 4.5%, not more than 4.25%, not more than 4.0%, not more than 3.75%, not more than 3.5%, not more than 3.25%, or lesser or intermediate percentages of sodium tetraborate decahydrate. Through this specification and claims where reference is made to sodium tetraborate decahydrate, a stoichiometrically equivalent amount of a different borate salt can be substituted as an equivalent.

In some embodiments the PC comprises at least 0.05%, at least 0.1%, at least 0.25%, at least 0.5%, at least 0.75%, at least 1.0% propolis or intermediate or greater percentages of propolis. Alternatively or additionally, in some embodiments the PC comprises not more than 1.25%, not more than 1.0%, not more than 0.75%, not more than 0.5%, not more than 0.25%, not more than 0.2%, not more than 0.15%, not more than 0.1%, or lesser or intermediate percentages of propolis.

In some embodiments the PC comprises at least 0.05%, at least 0.1%, at least 0.25%, at least 0.5%, at least 0.75%, at least 1.0% *Echinacea* sp. tincture or intermediate or greater percentages of *Echinacea* sp. tincture. Alternatively or additionally, in some embodiments the PC comprises not more than 1.25%, not more than 1.0%, not more than 0.75%, not more than 0.5%, not more than 0.25%, not more than 0.2%, not more than 0.15%, not more than 0.1%, or lesser or intermediate percentages of *Echinacea* sp. tincture.

According to another aspect of some embodiments of the invention glycerin (or another edible polyol) is heated to facilitate dissolution of sodium borate (e.g. sodium tetraborate decahydrate) therein and then cooled to facilitate dispersion of a broad spectrum antibiotic (e.g. tetracycline or a member of the tetracycline family) therein. According to various exemplary embodiments of the invention Calendula oil and/or Propolis and/or *Echinacea* sp. tincture and/or ethanol are the dispersed in the glycerin. According to various exemplary embodiments of the invention the amounts of the various ingredients are as set forth above in the context of the PC.

According to yet another aspect of some embodiments of the invention a dosing regimen for the PC includes administering 15 ml to 45 ml per day of the PC to a subject in need thereof. In some embodiments the total volume is divided into 5 to 7 portions. In some embodiments some of the portions are administered buccally. In some embodiments the portions vary in size. In some embodiments portions administered buccally are smaller than other portions. Alternatively or additionally, in some embodiments the dosing regimen includes 2 buccal portions per day.

According to still another aspect of some embodiments of the invention a method of treatment provides symptomatic relief for a covid-19 patient. The method includes administering to a COVID-19 patient a physiologically effective amount of a pharmaceutical composition comprising as active ingredients a tetracycline family antibiotic, Calendula oil, Propolis and *Echinacea* sp. tincture.

According to still another further aspect of some embodiments of the invention pharmaceutical composition comprising as active a tetracycline family antibiotic, Calendula oil, Propolis and *Echinacea* sp. tincture for use in the treatment of COVID-19.

It will be appreciated that the various aspects described above relate to solution of technical problems associated with treatment of COVID-19 symptoms.

Alternatively or additionally, it will be appreciated that the various aspects described above relate to solution of technical problems associated with reducing the burden on the health care system during the COVID-19 pandemic.

In some exemplary embodiments of the invention there is provided a pharmaceutical composition comprising: (a) a tetracycline family antibiotic, sodium tetraborate decahydrate, Calendula oil, Propolis, *Echinacea* sp tincture; and (b) a liquid carrier comprising glycerin and ethanol. In some embodiments, the tetracycline family antibiotic is selected from the group consisting of Tetracycline, Doxycycline and/or Oxytetracycline and/or Chlortetracycline and/or other Chemically Modified Tetracyclines. Alternatively or additionally, in some embodiments the composition includes at least 0.1% of the tetracycline family antibiotic. Alternatively or additionally, in some embodiments the composition includes not more than 2% of the tetracycline family antibiotic. Alternatively or additionally, in some embodiments the composition includes at least 3% of the sodium tetraborate decahydrate. Alternatively or additionally, in some embodiments the composition includes not more than 5% of the sodium tetraborate decahydrate. Alternatively or additionally, in some embodiments the composition includes at least 0.05% of the propolis. Alternatively or additionally, in some embodiments the composition includes not more than 0.2% of the propolis. Alternatively or additionally, in some embodiments the composition includes at least 0.05% *Echinacea* sp. tincture. Alternatively or additionally, in some embodiments the composition includes not more than 0.2% *Echinacea* sp. tincture.

In some exemplary embodiments of the invention there is provided a manufacturing process including: (a) heating glycerin to a temperature of 65° C. to 80° C.; (b) adding sodium borate and mixing till the sodium borate dissolves in the heated glycerin; (c) cooling the mixture to room temperature and dispersing a tetracycline family antibiotic in the mixture. In some embodiments the process includes dispersing in the mixture Calendula oil, Propolis, *Echinacea* sp. tincture and ethanol.

In some exemplary embodiments of the invention there is provided a dosing regimen including administering 15 ml to 45 ml per day of one or more of the pharmaceutical compositions set forth above to a subject in need thereof. In some embodiments the dosing regimen includes administering the 15 ml to 45 ml per day in 5 to 7 portions during the day. Alternatively or additionally, in some embodiments some of the portions are administered buccally. Alternatively or additionally, in some embodiments some of the portions are administered orally. Alternatively or additionally, in some embodiments not all of the portions are equivalent in size. Alternatively or additionally, in some embodiments portions administered buccally are smaller than other portions. Alternatively or additionally, in some embodiments the buccal portions are administered twice daily. Alternatively or additionally, in some embodiments the subject in need thereof is suffering from symptoms of COVID-19.

In some exemplary embodiments of the invention there is provided a method of treatment comprising: administering to a COVID 19 patient a physiologically effective amount of a pharmaceutical composition comprising as active ingredients a tetracycline family antibiotic, Calendula oil, Propolis and *Echinacea* sp. tincture.

In some exemplary embodiments of the invention there is provided a pharmaceutical composition comprising as active ingredients a tetracycline family antibiotic, Calendula oil, Propolis and *Echinacea* sp. tincture for use in the treatment of Covid 19.

Unless otherwise defined, all technical and scientific terms used herein have the same meaning as commonly understood by one of ordinary skill in the art to which this invention belongs. Although suitable methods and materials are described below, methods and materials similar or equivalent to those described herein can be used in the practice of the present invention. In case of conflict, the patent specification, including definitions, will control. All materials, methods, and examples are illustrative only and are not intended to be limiting.

For purposes of this specification and the accompanying claims, the term "*Echinacea* sp." indicates *Echinacea angustifolia* and/or *Echinacea purpurea* and/or any other medically useful species of *Echinacea*.

As used herein, the terms "comprising" and "including" or grammatical variants thereof are to be taken as specifying inclusion of the stated features, integers, actions or components without precluding the addition of one or more additional features, integers, actions, components or groups thereof. This term is broader than, and includes the terms "consisting of" and "consisting essentially of" as defined by the Manual of Patent Examination Procedure of the United States Patent and Trademark Office. Thus, any recitation that an embodiment "includes" or "comprises" a feature is a specific statement that sub embodiments "consist essentially of" and/or "consist of" the recited feature.

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

The phrase "adapted to" as used in this specification and the accompanying claims imposes additional structural limitations on a previously recited component.

The term "method" refers to manners, means, techniques and procedures for accomplishing a given task including, but not limited to, those manners, means, techniques and procedures either known to, or readily developed from known manners, means, techniques and procedures by practitioners of architecture and/or computer science.

Percentages (%) are W/V (weight per volume) unless otherwise indicated. For example, 1% indicates 1 g per 100 ml.

BRIEF DESCRIPTION OF THE DRAWINGS

In order to understand the invention and to see how it may be carried out in practice, embodiments will now be described, by way of non-limiting example only, with reference to the accompanying figures. In the figures, identical and similar structures, elements or parts thereof that appear in more than one figure are generally labeled with the same or similar references in the figures in which they appear. Dimensions of components and features shown in the figures are chosen primarily for convenience and clarity of presentation and are not necessarily to scale. The attached figures are.

DETAILED DESCRIPTION OF EMBODIMENTS

Figure 1:
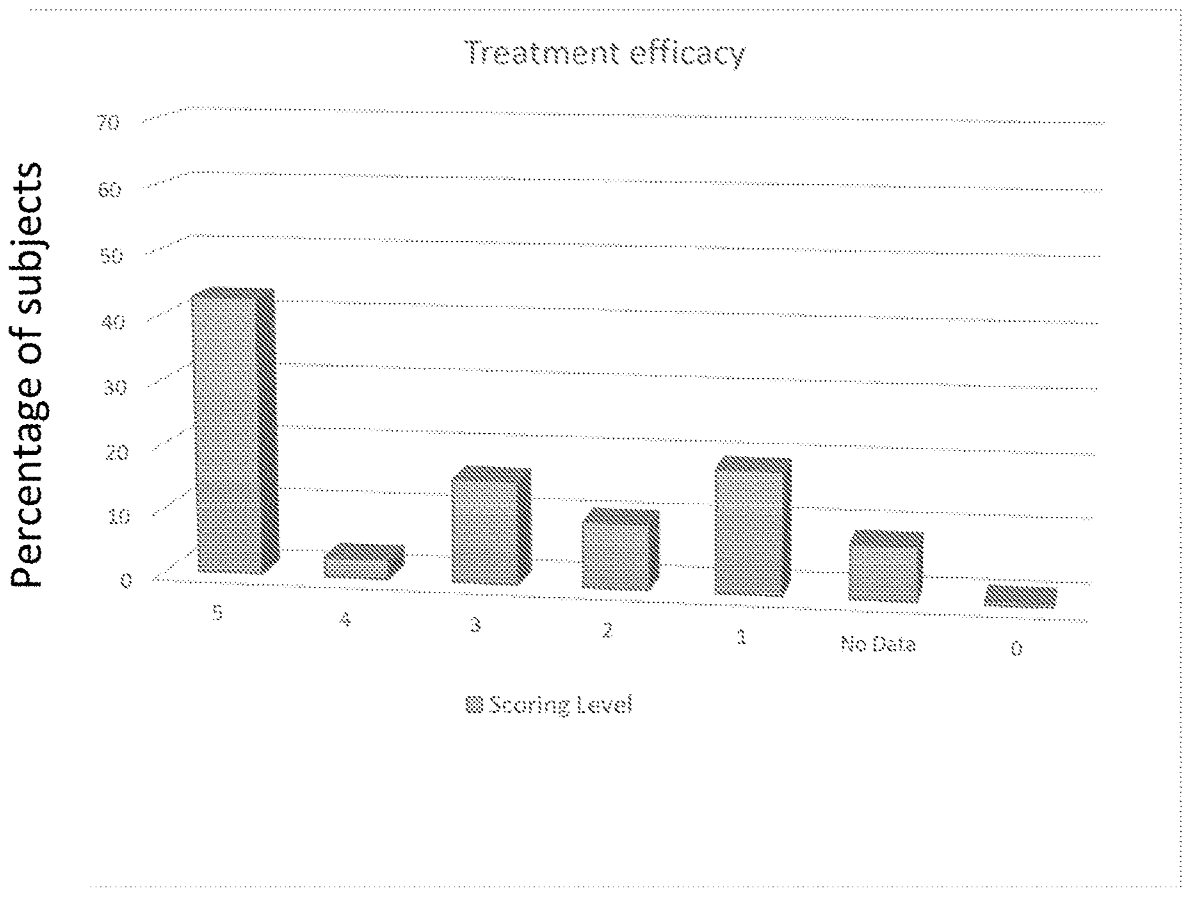
FIG. 1 is bar graph of percentage of COVID-19(+) patient percentage as a function of scoring level.

Embodiments of the invention relate to pharmaceutical compositions (PC) and methods of making and using them.

Specifically, some embodiments of the invention can be used to relive symptoms of COVID-19.

The principles and operation of a PC and/or method according to exemplary embodiments of the invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Exemplary Pharmaceutical Compositions

In some exemplary embodiments of the invention, relate to a pharmaceutical composition (PC) comprising: a tetracycline family antibiotic, sodium tetraborate decahydrate, Calendula oil, Propolis, *Echinacea* sp. tincture; and a liquid carrier comprising glycerin (or another edible polyol) and ethanol (e.g. 1% to 4% W/V). According to various exemplary embodiments of the invention the tetracycline family antibiotic includes Tetracycline and/or Doxycycline and/or Oxytetracycline and/or Chlortetracycline and/or other chemically modified Tetracyclines. Alternatively or additionally, in some embodiments the PC includes at least 0.1% of said tetracycline family antibiotic and/or includes not more than 2% of said tetracycline family antibiotic. In some exemplary embodiments of the invention, the PC includes at least 3% and/or not more than 5% of sodium tetraborate decahydrate (or stoichiometric equivalent of another borate salt). In some exemplary embodiments of the invention, the PC includes at least 0.05% and/or not more than 0.2% of propolis. In some exemplary embodiments of the invention, the PC includes at least 0.05% and/or not more than 0.2% *Echinacea* sp tincture.

Exemplary Manufacturing Process

Some exemplary embodiments of the invention relate to a manufacturing process comprising heating glycerin to a temperature of 65° C. to 80° C., adding sodium borate and mixing till the sodium borate dissolves in the heated glycerin, cooling the mixture to room temperature and dispersing a tetracycline family antibiotic in the mixture. In some exemplary embodiments of the invention, the process includes dispersing in the mixture Calendula oil and/or Propolis and/or *Echinacea* sp. tincture and/or ethanol. According to various exemplary embodiments of the invention the amounts of these ingredients are as detailed hereinabove for exemplary PCs. (e.g. in the summary of invention)

Exemplary Dosing Regimens

Some exemplary embodiments of the invention relate to a dosing regimen comprising administering 15 ml to 45 ml per day of a pharmaceutical composition as described hereinabove to a subject in need thereof. In some embodiments a subject in need thereof has tested (+) for COVID-19 and/or exhibits symptoms of COVID-19 infection. In some embodiments the dosing regimen includes administering the 15 ml to 45 ml per day in 5 to 7 portions during the day. In some embodiments, some of the portions are administered buccally. In some embodiments, some of the portions are administered orally. In some embodiments, not all of the portions are equivalent in size. In some embodiments, portions administered buccally are smaller than other portions. In some embodiments, the buccal portions are administered twice daily.

Exemplary Treatment Method

Some exemplary embodiments of the invention relate to a method of treatment comprising administering to a COVID 19 patient a physiologically effective amount of a pharmaceutical composition comprising as active ingredients a tetracycline family antibiotic, Calendula oil, Propolis and *Echinacea* sp. tincture.

Amounts of active ingredients and carriers are as explained above in context of pharmaceutical compositions (e.g. in the summary of invention). For purposes of this specification and the accompanying claims, the term "physiologically effective" indicates relief of symptoms as evaluated by the subject.

Exemplary Medical Use

Some exemplary embodiments of the invention relate to a pharmaceutical composition comprising as active ingredients a tetracycline family antibiotic, Calendula oil, Propolis and *Echinacea* sp. tincture for use in the treatment of Covid 19. Amounts of active ingredients and carriers are as explained above in context of pharmaceutical compositions (e.g. in the summary of invention).

Exemplary Manufacturing Protocol

For preparing a total volume of 1 Liter.

Materials:

Vegetable Glycerin oil—850 ml.

Sodium tetraborate decahydrate—40 gr.

Calendula oil, 30% (1:3)—84 ml.

Propolis block in Ethanol tincture (1:10)—12.6 ml.

*Echinacea* Ang. in Ethanol tincture (1:3)—12.6 ml.

Tetracycline HCl.—1,250 mg.

The final concentration of Calendula oil is 10% and the 1:3 dilution is done with soybean oil or another edible oil such as canola oil or corn oil. The Calendula oil itself was purchased from Duellberg-Konzentra (Hamburg, Germany Cat-1001685)

The Propolis block was diluted in ethanol to produce the tincture. Propolis was obtained from Bara-Herbs (Yokneam, Israel; Cat no. T-8-2650-1000). The expression 1:10 indicates 1 g propolis in 10 mL ethanol.

The *Echinacea* Ang. Bara-Herbs (Yokneam, Israel; Cat no. T-08-2593-1000) tincture was prepared by soaking 1 g of plant material in 3 ml of ethanol.

In order to prepare the final mixture glycerin was heated to 73° C. in a heating bath or on a heating plate with a stirrer. Sodium tetraborate was added and mixed until complete dissolution producing a clear liquid. This typically took 20 minutes or more. The mixture was then cooled to 25-30° C. the remaining materials were added with stirring until the mixture is fully homogenous. Tetracycline powder was added gradually to prevent the formation of lumps. The final mixture (Respiztal) was allowed to stand undisturbed at room temperature protected from light for 72 hours.

For cell culture experiments a mixture without tetracycline was prepared as a control.

It is expected that during the life of this patent many additional tetracycline family antibiotics will be developed and the scope of the invention is intended to include all such new technologies a priori.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

Specifically, a variety of numerical indicators have been utilized. It should be understood that these numerical indicators could vary even further based upon a variety of engineering principles, materials, intended use and designs incorporated into the various embodiments of the invention. Additionally, components and/or actions ascribed to exemplary embodiments of the invention and depicted as a single unit may be divided into subunits. Conversely, components and/or actions ascribed to exemplary embodiments of the invention and depicted as sub-units/individual actions may be combined into a single unit/action with the described/depicted function.

Alternatively, or additionally, features used to describe a method can be used to characterize an apparatus and features used to describe an apparatus can be used to characterize a method.

It should be further understood that the individual features described hereinabove can be combined in all possible combinations and sub-combinations to produce additional embodiments of the invention. The examples given above are exemplary in nature and are not intended to limit the scope of the invention which is defined solely by the following claims.

Each recitation of an embodiment of the invention that includes a specific feature, part, component, module or process is an explicit statement that additional embodiments of the invention not including the recited feature, part, component, module or process exist.

Alternatively or additionally, various exemplary embodiments of the invention exclude any specific feature, part, component, module, process or element which is not specifically disclosed herein. COVID-19 but might also be used in the context of related viruses.

All publications, references, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The terms “include”, and “have” and their conjugates as used herein mean “including but not necessarily limited to”.

Additional objects, advantages, and novel features of various embodiments of the invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non-limiting fashion.

Materials and Methods

The following materials and methods are used in performance of experiments described in examples hereinbelow:

Borax (sodium borate): Santa Cruz Biotechnology, Inc. Santa Cruz, California, cat: sc-212947

Tetracycline: Santa Cruz Biotechnology, Inc. Santa Cruz, California, cat: sc-205858D Calendula oil: Duellberg-Konzentra (Hamburg, Germany Cat-1001685)

Propolis: Bara-Herbs (Yokneam, Israel; Cat no. T-8-2650-1000)

*Echinacea angustifolia* tincture: Bara-Herbs (Yokneam, Israel; Cat no. T-08-2593-1000)

Example 1

Exemplary Pharmaceutical Composition

In order to perform in vitro studies in cell lines and perform an initial assay of efficacy in human subjects, the following pharmaceutical composition was prepared.

in 1 liter of food grade glycerin:

Borax (sodium borate)—60 gr

Tetracycline—1,500 mg

Calendula oil (1:10)—100 cc, 10 cc active amount

Propolis—1.5 gr

*Echinacea angustifolia* tincture—1.5 gr

Ethanol 32%—30 gr.

Example 2

Study in Human Subjects

In order to evaluate the efficacy of the composition of example 1 in providing symptomatic relief from COVID-19, human subjects with relevant symptoms were recruited. Some of these subjects tested (+) and others tested (−) in a PCR test based on nasal/oral swabs. All were treated with the composition of Example 1.

Patients were given 5 ml of the composition orally five times a day at three hour intervals. Additionally, twice a day, morning and evening, the patients were given 2.5 ml under the tongue (buccal administration). Patients were instructed not to eat or drink for twenty minutes after taking the dose, and to refrain from dairy products.

The outcome of the treatment was characterized according to the following five scoring levels, ranging from a swift and very significant improvement, to no improvement and finally worsening of the patient conditions:

5=Immediate and Substantial Improvement.

4=Substantial Improvement.

3=Medium Improvement.

2=Some Improvement.

1=No Improvement.

0=Worsening.

In addition, the time it took for a patient to start to exhibit the recorded improvement was recorded, and ranged from an immediate relief to a relief after 3 days of treatment. Results are summarized in Table 1.

TABLE 1

Summary of improvement and time to improvement in human subjects treated with a pharmaceutical composition according to an exemplary embodiment of the invention

| Patient Group | number | Improvement score Mean | Days to improvement Mean† |
|---|---|---|---|
| COVID-19 (+) | 154 | 3.42 | 1.48 |

†data available from only 121 patients since those with score of 1 or 0 had no improvement Results presented in Table 1 illustrate that, on average, a PC according to an exemplary embodiment of the invention provided a "medium improvement" in symptoms in about 1.5 days.

FIG. 1 is a graphic summary of the patient data giving the results in terms of percentages. FIG. 1 shows that 46% of the patients had a substantial improvement (43% score 5 plus 3% score 4) and 26% exhibited medium to some improvement (16% score 3 plus 10% score 2), bringing the success rate of the treatment to 72%.

This example suggests that a PC according to an exemplary embodiment of the invention has anti COVID-19 activity and/or modulate immune system activity.

Example 3

In Vitro Efficacy Assay

In order to separate the effect of antibiotic such as tetracycline from other ingredients in the formulation, a direct comparison was conducted in cell culture.

MRC-5 (lung fibroblast cell line) cells were placed on 96 well plates, in their culture medium, at 1×104 cells/well and allowed to attach for 16-24 hours at 37° C., 5% CO2. Culture medium was discarded, and 100 μL of assay media was added to the cells, supplemented with test material, as detailed below the X axis of FIG. 2 and according to the nontoxic concentration determined previously.

The cells were incubated with test material for 4 hours at 37° C., 5% CO2 before 1 μL of assay media of virus at 100 times the infective dose was added to the cells. The cells were incubated for additional 72±2 hours at 37° C., 5% CO2.

At the end of the incubation period, assay media was discarded, and fresh culture medium was added to the cells with 50 μL of XTT reagent. XTT reagent is a colorimetric reagent which facilitates a colorimetric assay for quantification of cellular proliferation, viability, and cytotoxicity. The OD was measured using a plate reader once Vehicle treated cells reached the range of 0.5-1.5 OD at 450 nm wavelength (after subtraction of the non-specific OD at 620 nm).

Pyrazofurin (5 μg/ml) served as a positive control for antiviral activity.

Figure 2:
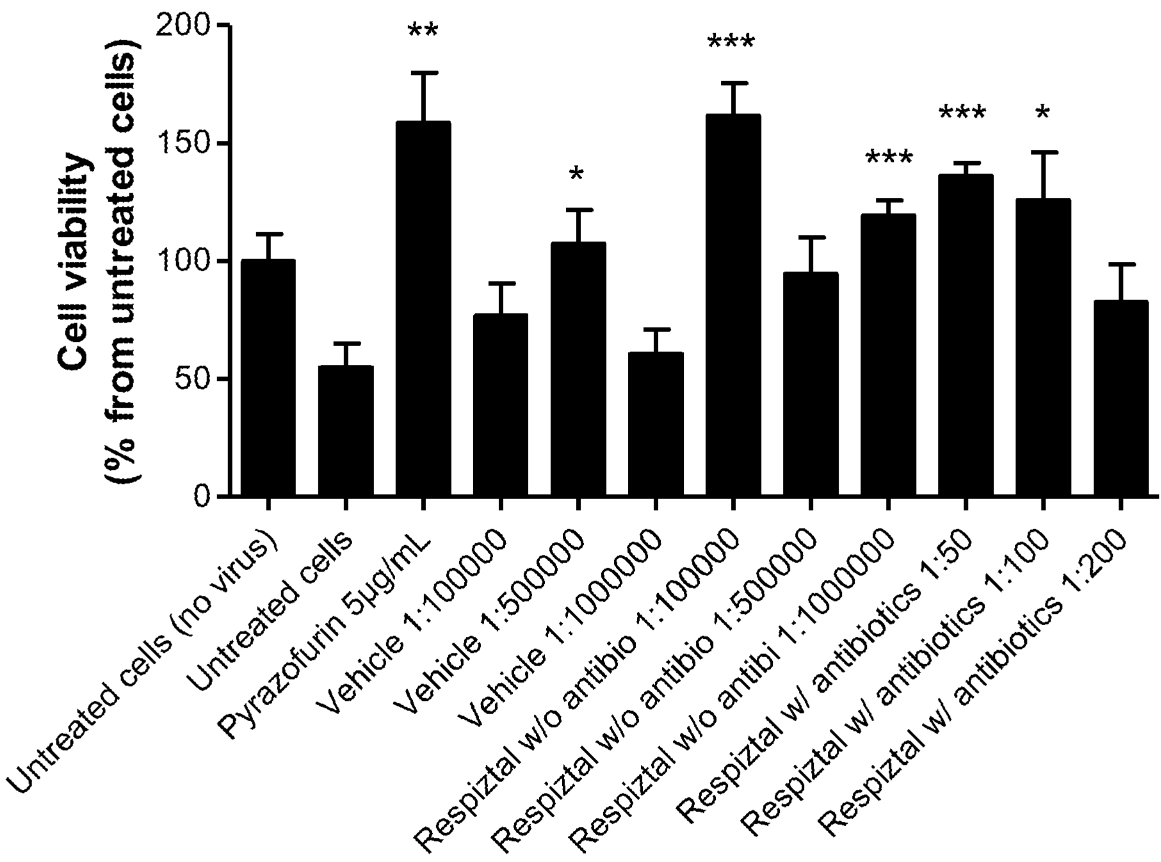
FIG. 2 is bar graph of cell viability percentage as a function of test material in an MRC-5 cell culture assay.

Results summarized graphically in FIG. 2 indicate that the formula (Respiztal) shows a protective effect on cells in culture and rescues the cells from cell death after infection with Human corona virus 229E.

The formula showed a high toxicity without the antibiotics. Adding the tetracycline facilitated an increase in the dose of other ingredients of the formula without the toxic effect. In other words, the data suggest that Tetracycline in the formula exerts a protective effect on cells, a finding which is consistent with the scientific literature.

Asterisks indicate level of significance for each treatment compared to untreated (with virus) cells, according to t-Test as follows: *$p<0.05$, $p<0.01$, *$p<0.001$ This example suggest that the ingredients of the formula protect human cells from viral infection and explain the significant relief of the symptoms presented in the study of example 2.

The invention claimed is:

1. A method of treatment comprising:

administering to a COVID 19 patient a physiologically effective amount of a pharmaceutical composition comprising as active ingredients a tetracycline family antibiotic, Calendula oil, Propolis and *Echinacea* sp. tincture.

2. The method of claim 1, wherein said active ingredients in said pharmaceutical composition consist essentially of said tetracycline family antibiotic, said Calendula oil, said Propolis and said *Echinacea* sp. Tincture.

3. The method of claim 2, wherein said active ingredients in said pharmaceutical composition consist of said tetracycline family antibiotic, said Calendula oil, said Propolis and said *Echinacea* sp. Tincture.

* * * * *